US010114453B2

United States Patent
Tanaka et al.

(10) Patent No.: US 10,114,453 B2
(45) Date of Patent: Oct. 30, 2018

(54) SMART WEARABLE DEVICES AND METHODS WITH POWER CONSUMPTION AND NETWORK LOAD OPTIMIZATION

(71) Applicants: SONY CORPORATION, Tokyo (JP); SONY CORPORATION OF AMERICA, New York, NY (US)

(72) Inventors: Nobuo Tanaka, Glen Rock, NJ (US); Vladimir Elgort, Staten Island, NY (US); Jacelyn Danielson, San Mateo, CA (US); Anton Kalachev, Burlingame, CA (US); John Wong, Morristown, NJ (US); Behram DaCosta, San Jose, CA (US); Udupi Ramanath Bhat, Mountain View, CA (US); Ludovic Copere, San Jose, CA (US); Masaki Kataoka, Port Washington, NY (US)

(73) Assignees: SONY CORPORATION, Tokyo (JP); SONY CORPORATION OF AMERICA, New York, NY (US)

( * ) Notice: Subject to any disclaimer, the term of this patent is extended or adjusted under 35 U.S.C. 154(b) by 166 days.

(21) Appl. No.: 15/236,461

(22) Filed: Aug. 14, 2016

(65) Prior Publication Data

US 2017/0010658 A1    Jan. 12, 2017

Related U.S. Application Data

(63) Continuation of application No. PCT/US2015/016590, filed on Feb. 19, 2015.

(Continued)

(51) Int. Cl.
*G06F 3/01* (2006.01)
*G06F 1/16* (2006.01)
(Continued)

(52) U.S. Cl.
CPC .............. *G06F 3/011* (2013.01); *G06F 1/163* (2013.01); *G06F 1/1637* (2013.01);
(Continued)

(58) Field of Classification Search
CPC .... G06F 19/3418; G06F 1/1626; G06F 1/163; G06F 1/1637; G06F 1/1698;
(Continued)

(56) References Cited

U.S. PATENT DOCUMENTS 9,619,010 B1 *   4/2017   Marathe ................ G06F 1/3287
9,867,125 B2 *   1/2018   Eremenko ......... H04W 52/0203
(Continued)

FOREIGN PATENT DOCUMENTS

EP    1 314 102 B1     4/2001
JP    2014-12072 A     1/2014
(Continued)

OTHER PUBLICATIONS

Japan Patent Office (JPO), Preliminary Notice of Reasons for Refusal dated Sep. 11, 2017, related Japanese application No. 2016-551264, pp. 1-3, English-language translation, pp. 4-5, with claims examined, pp. 6-11.

(Continued)

*Primary Examiner* — Tony Davis
(74) *Attorney, Agent, or Firm* — O'Banion & Ritchey LLP; John P. O'Banion (57) ABSTRACT

Networked smart wearable devices and methods for dynamic power management of multiple wearable devices and the optimization of the network sensor data load through network control of the sensors in each wearable device is provided.

17 Claims, 4 Drawing Sheets

Related U.S. Application Data (60) Provisional application No. 61/943,837, filed on Feb. 24, 2014.

(51) Int. Cl.
*G06F 1/32* (2006.01)
*G06F 19/00* (2018.01)
*H04L 29/06* (2006.01)
*H04W 12/06* (2009.01)
*G16H 40/63* (2018.01)
*G08B 7/00* (2006.01)

(52) U.S. Cl.
CPC ............ *G06F 1/1698* (2013.01); *G06F 1/325* (2013.01); *G06F 1/3206* (2013.01); *G06F 1/3287* (2013.01); *G06F 3/015* (2013.01); *G06F 3/016* (2013.01); *G06F 19/00* (2013.01); *G06F 19/3418* (2013.01); *G16H 40/63* (2018.01); *H04L 63/0861* (2013.01); *H04L 63/0869* (2013.01); *H04W 12/06* (2013.01); *G06F 1/1626* (2013.01); *G08B 7/00* (2013.01); *Y02D 10/171* (2018.01)

(58) Field of Classification Search
CPC ...... G06F 1/3206; G06F 1/325; G06F 1/3287; G06F 3/011; G06F 3/015; G06F 3/016; G08B 7/00; H04L 63/0861; H04L 63/0869; H04W 12/06; Y02D 10/171
USPC .......................................... 345/156, 169–173
See application file for complete search history.

(56) References Cited

U.S. PATENT DOCUMENTS

| | | | |
|---|---|---|---|
| 2001/0043514 A1* | 11/2001 | Kita ..................... | A44C 5/0015 368/281 |
| 2001/0047127 A1* | 11/2001 | New, Jr. ............... | A61B 5/0002 600/300 |
| 2002/0084901 A1 | 7/2002 | Mantyjarvi et al. | |
| 2007/0279852 A1* | 12/2007 | Daniel .................. | A44C 5/0007 361/679.03 |
| 2009/0026839 A1* | 1/2009 | Drageset ............... | G06F 1/263 307/32 |
| 2009/0131759 A1* | 5/2009 | Sims .................... | A61B 5/1135 600/301 |
| 2009/0171180 A1 | 7/2009 | Pering | |
| 2010/0298742 A1* | 11/2010 | Perlman ................ | A61B 5/1116 600/595 |
| 2011/0213217 A1 | 9/2011 | McKenna et al. | |
| 2011/0214158 A1* | 9/2011 | Pasquero .............. | G06F 21/35 726/2 |
| 2012/0007432 A1* | 1/2012 | Rice .................... | H02J 1/00 307/82 |
| 2012/0149301 A1* | 6/2012 | Wiley .................. | H04B 5/0031 455/41.1 |
| 2012/0249741 A1* | 10/2012 | Maciocci .............. | G06F 3/011 348/46 |
| 2013/0096466 A1 | 4/2013 | Sarrafzadeh et al. | |
| 2013/0285836 A1 | 10/2013 | Proud | |
| 2013/0311132 A1 | 11/2013 | Tobita | |
| 2014/0012146 A1 | 1/2014 | Fukuda | |
| 2014/0052567 A1* | 2/2014 | Bhardwaj .......... | G06Q 30/0631 705/26.7 |
| 2014/0215242 A1* | 7/2014 | Jung ................... | G06F 9/4893 713/322 |
| 2015/0057967 A1* | 2/2015 | Albinali ............... | A61B 5/1118 702/150 |
| 2015/0170504 A1* | 6/2015 | Jooste ................. | A61B 5/6898 340/539.12 |
| 2015/0177811 A1* | 6/2015 | Bose .................... | G06F 1/3287 713/324 |
| 2015/0179050 A1* | 6/2015 | Katingari .............. | G08B 25/10 340/539.13 |
| 2015/0185839 A1* | 7/2015 | Magi .................... | G06F 3/014 345/173 |
| 2015/0277401 A1* | 10/2015 | Hsiao ................... | G05B 15/02 700/40 |
| 2015/0277540 A1* | 10/2015 | Jackson ................ | G06F 1/3265 345/169 |
| 2015/0373723 A1* | 12/2015 | Zhang .................. | H04L 47/29 370/311 |
| 2015/0379963 A1* | 12/2015 | Holmanu ............. | G09G 5/12 345/173 |
| 2016/0044151 A1* | 2/2016 | Shoemaker ........... | H04M 19/04 455/556.1 |
| 2016/0057511 A1* | 2/2016 | Mullins ................ | G08C 17/00 340/870.07 |
| 2016/0064955 A1* | 3/2016 | Zuerner ................ | H02J 7/007 705/39 |
| 2016/0094936 A1* | 3/2016 | Yang .................... | H04Q 9/00 455/456.1 |
| 2016/0277891 A1* | 9/2016 | Dvortsov .............. | H04W 4/008 |
| 2016/0284210 A1* | 9/2016 | Wang ................... | G08C 17/02 |
| 2017/0013558 A1* | 1/2017 | Li ........................ | G01R 31/362 |
| 2017/0156667 A1* | 6/2017 | Lerner ................. | A61B 5/6803 |
| 2017/0164291 A1* | 6/2017 | Ludwig ............. | H04W 52/0254 |

FOREIGN PATENT DOCUMENTS

| | | |
|---|---|---|
| KR | 10-2011-0056332 A | 5/2011 |
| WO | 2010/033191 A1 | 3/2010 |
| WO | 2013/096954 A1 | 6/2013 |

OTHER PUBLICATIONS

European Patent Office (EPO), extended European search report dated Oct. 26, 2017, related European application No. 15752742.5, pp. 1-8, with claims searched, p. 9-12.

United States Patent and Trademark Office (USPTO), International Search Report and Written Opinion, PCT International Application No. PCT/US2015/016590, dated May 22, 2015, pp. 1-10, with claims searched, pp. 11-16.

Popescu et al., "An Acoustic Fall Detector System that Uses Sound Height Information to Reduce the False Alarm Rate", 30 Annual International IEEE Conference, Vancouver, British Columbia, Canada, Aug. 20-24, 2008, pp. 4628-4631.

Korean Intellectual Property Office (KIPO), Notice of Last Preliminary Rejection dated Mar. 30, 2018, related Korean patent application No. 10-2016-7021757, Korean-language office action pp. 1-9, English-language translation pp. 10-18, English-language claims examined pp. 19-22.

* cited by examiner

SMART WEARABLE DEVICES AND METHODS WITH POWER CONSUMPTION AND NETWORK LOAD OPTIMIZATION

CROSS-REFERENCE TO RELATED APPLICATIONS

This application is a 35 U.S.C. § 111(a) continuation of PCT international application number PCT/US2015/016590 filed on Feb. 19, 2015, incorporated herein by reference in its entirety, which claims priority to, and the benefit of, U.S. provisional patent application Ser. No. 61/943,837 filed on Feb. 24, 2014, incorporated herein by reference in its entirety. Priority is claimed to each of the foregoing applications.

The above-referenced PCT international application was published as PCT International Publication No. WO 2015/127056 A2 on Aug. 27, 2015, which publication is incorporated herein by reference in its entirety.

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Field of the Technology

This technology pertains generally to smart wearable devices and sensor networks and more particularly to a system of networked wearable sensor and processing devices with dynamic power consumption and network load optimization.

2. Discussion

Current wearable devices are typically autonomous and the device architecture is not capable of communicating with other wearable devices. For example, sensor data from a sensor wristband worn by a wearer would not take into consideration other wearable devices such as smart-glasses that may be coincidentally present on or around the same body of a user. Emerging markets for wearable devices means that most wearers will not be limited to the use of only a single device at a given time. Rather, with the availability of reasonably priced wearable devices, many users will be able to wear a number of wearable devices simultaneously.

However, the isolated sensing of each wearable sensor device results in the very inefficient management of the total "sensing" and "computing" pool of resources of the set of multiple wearable devices. There is no control over the redundant sensors that could remain idle during this period. For example, duplicated sensing of the same body parameter (e.g. heart-rate or skin temperature) may be occurring from multiple wearable devices at the same time, whereas a single reading from any one of them would provide enough sensor data.

Accordingly, the lack of control and redundancy creates sub-optimal power consumption and reduces the overall battery life of all of the wearable devices (as they could be "sleeping" or remaining idle instead of capturing data needlessly), as well as network load (as those same wearable devices may be uploading redundant sensed data to multiple remote/Cloud-based locations which have no possible knowledge of those multiple occurrences).

Increasing the battery life of wearable devices is a concern to users of such devices. Recharging requirements of wearable sensors in a watch, glasses or clothing item influences the overall usefulness of the wearable device. Reducing the number of recharge cycles in a given time period will also make the wearable devices more "wearer-friendly."

The transfer load of sensor data from isolated wearable sensor devices is also a concern with the growing number of wearable devices that are available. This is of particular interest to mobile network operators or other providers of the network capacity for "Machine-to-Machine" communications between wearable devices and remote/Cloud systems. Optimization of the amount of data would reduce the transfer load (and potential bandwidth crunch) given the fact that potentially thousands/millions of wearers may be uploading data concurrently.

Nevertheless, in some settings the acquisition of redundant sensor data is useful. For example, a body parameter may benefit from the combination of multiple readings (e.g. temperature at different locations throughout the body), which would be impossible to achieve right now despite the potential existence of multiple readings from the several wearable devices. While a casual jogger may be satisfied with a single tracker measuring the pace/heart-rate, a semi-pro or professional runner may want more precise measurements through the use of multiple devices.

There is a need for devices and methods for controlling the production and processing of sensor data and for the optimization of power consumption in each of the multiple wearable sensors worn by a user.

BRIEF SUMMARY

This disclosure describes smart wearable devices and methods for dynamic power management of multiple wearable devices and the optimization of the network sensor data load through network control of the sensors in each wearable device.

In one embodiment, the overall system apparatus has at least one base wearable device, multiple satellite devices and optional non-wearable or remote computation devices. Multiple satellite wearable sensor devices communicate with a base wearable device and are controlled by the base device. The base and satellite wearable devices generally comprise one or more sensors, a communications link and a computer processor with memory and programming.

A control hierarchy between wearable devices is created with a control classification so that control over one device by another is authorized and permitted based on the assigned classification. In this embodiment, new satellite or base wearable devices can be introduced and automatically integrated into the system.

The base wearable apparatus detects any satellite wearable devices that are within range of the communications link of the apparatus and then communicates with the detected devices. The control classifications of each of the detected satellite devices are identified and control is established based on the classifications of the satellite devices. Programming of the base also determines the sensors that are present in each detected device to determine redundancies. The control of the actuation and data flow of all of the sensors of all of the devices is consolidated to one base apparatus. The sensor data may be processed either at the satellite device, the base device or may be communicated to a remote computer or non-wearable device for processing and evaluation.

For instance, when queried, wearable device A would inform wearable device B that it can read a specific body parameter, with a certain sampling rate and with a certain accuracy. Wearable Device B could then have the power to temporarily "shut-down" wearable device A (or one of its sub-components) in case its own reading for this specific metric is better or more accurate, or in the case where multiple concurrent readings are unnecessary.

Additionally, the decision-making programming for control over the sensors of the wearable devices could either be done between the devices themselves with a base wearable sensor or the programming could involve an outside (remote/Cloud-based) decision engine which would be akin to an "equalizer" in audio/video applications. This equalizer would allow the amplification/neutralization of specific sensing for each wearable device worn by the same wearer. In one embodiment, the settings for such an equalizer could be either accessible by the user (allowing the user to choose between longer battery life and higher measuring performance) or could be remotely tweaked by 3rd-party applications on a remote computer.

Battery power availability of each satellite device is also monitored by the programming of the base device in one embodiment. The activity of redundant sensors and the production and transmission of redundant sensor data is also controlled by the programming of the base apparatus.

One embodiment accounts for the fact that many wearable devices are produced by different vendors/OEMs and each have proprietary APIs and methods to access or control the particular wearable device. In this embodiment, each vendor or OEM of wearable device will accept and embed an agnostic software layer. This would be beneficial on its own as each wearable device would operate more efficiently and with a longer battery life (so it would not diminish its unique merit or differentiation).

Each of the wearable devices integrates a vendor-neutral common (and possibly standardized) API which exposes their capacity to other neighboring wearable devices. This is independent of each wearable device's proprietary (and/or vendor-specific) sensing algorithm(s) which would remain untouched.

Further aspects of the technology will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only.

DETAILED DESCRIPTION

Referring more specifically to the drawings, for illustrative purposes an embodiment of a wearable apparatus and method for dynamic power consumption and network load optimization is described and depicted generally in FIG. 1 through FIG. 4. It will be appreciated that the methods may vary as to the specific steps and sequence and the apparatus may vary as to elements and structure without departing from the basic concepts as disclosed herein. The method steps are merely exemplary of the order in which these steps may occur. The steps may occur in any order that is desired, such that it still performs the goals of the claimed technology.

The present disclosure generally pertains to wearable devices that are capable of, for example, performing an action based on one or more biological or physiological characteristics of the user wearing the device. Using one or more sensors, a processor, and code executable on the processor, a wearable device can be configured to sense and process characteristics that include, but are not limited to, a wearer's physical characteristics such as gender, weight, height, body temperature, skin temperature, heart rate, respiration, blood sugar level, blood glucose level, stress/fatigue, galvanic skin response, ingestion (protein), digestion rate, metabolic rate, blood chemistry, sweat, core and skin temperature, vital signs, eye dryness, tooth decay, gum disease, energy storage, calorie burn rate, mental alertness, cardiac rhythm, sleep patterns, caffeine content, vitamin content, hydration, blood oxygen saturation, blood cortisol level, blood pressure, cholesterol, lactic acid level, body fat, protein level, hormone level, muscle mass, pH, etc. Such conditions may also include, but are not limited to, position (e.g., prone, upright), movement, or physical state (e.g., sleeping, exercising), etc.

A wearable device may include one or more output devices that include, but are not limited to, haptic output devices (e.g., offset motors, electroactive polymers, capacitive voltage generators, Peltier temperature elements, contracting materials, Braille coding actuators), telemetry devices, visual devices, audible devices, and other output devices.

A wearable device may also include artificial intelligence so that the device can learn and adapt to the wearer. The device may be configured to accurately discriminate between erroneous (accidental, unintended, etc.) and valid sensory inputs, thereby developing accurate conclusions about a wearer's physical state or characteristics (e.g., the device does not interpret a wearer rolling over in their sleep as the wearer exercising). The device may also include one or more cameras or other visual sensors for facial, user, or other image recognition. A wearable device may also be configured to transmit information to and/or retrieve information from a wearer's digital health history.

A wearable device may be configured to output information to a user, to another wearable device, to a non-wearable device, or to a network according to the particular features and function of the device.

A. Generalized System Implementation.

Figure 1:
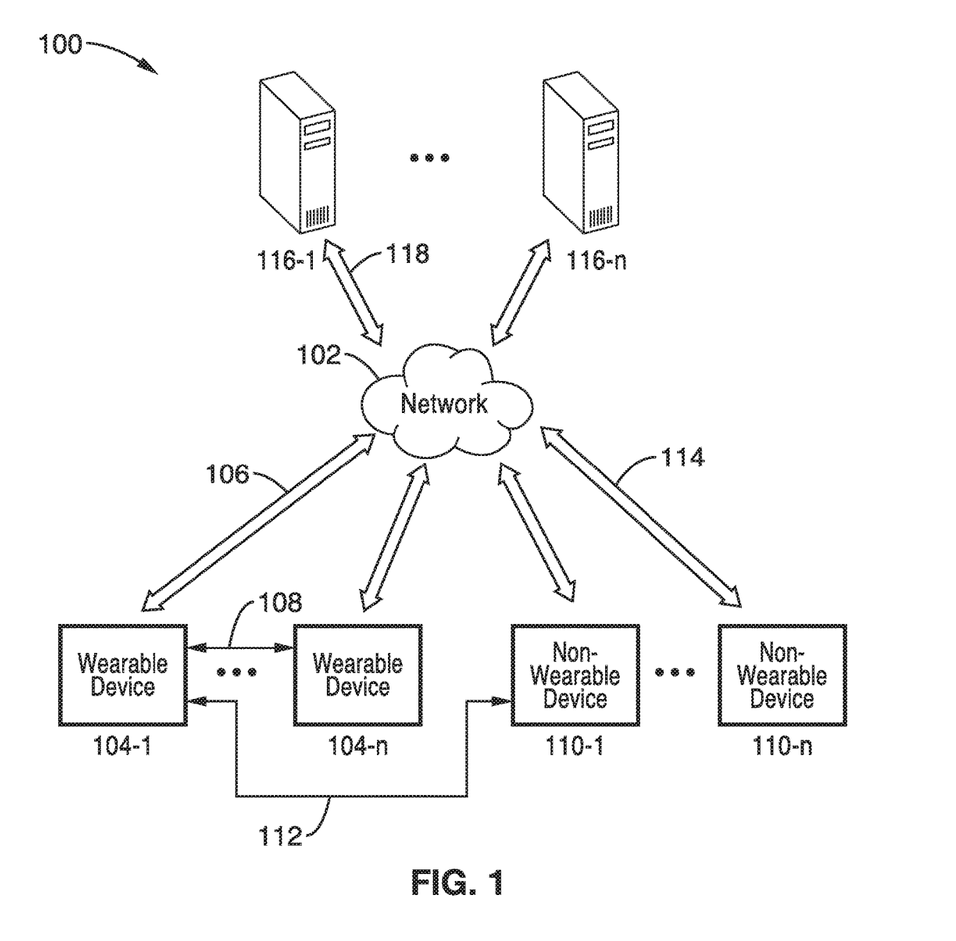
FIG. 1 is a schematic diagram of an embodiment of a smart wearable network described herein.

FIG. 1 illustrates a generalized networked infrastructure (e.g., system) 100 that includes a network 102. The network could, for example, be a local area network or a wide area network such as the Internet. One or more smart wearable devices 104-1 through 104-n according to embodiments of the technology described herein may be enabled to communicate with the network 102 through a wired or wireless connection 106. Further, one or more of the smart wearable devices may be enabled to communicate with another smart wearable device through the network 102 or by means of a direct wired or wireless connection 108.

One or more of the smart wearable devices 104-1 through 104-n also may be enabled to communicate with one or more non-wearable devices 110-1 through 110-n. The non-wearable devices, which are beyond the scope of this disclosure, may be any conventional "smart" device with a processor, associated operating system, and communications interface. Examples of non-wearable devices include Smartphones, tablet computers, laptop computers, desktop computers, and set top boxes. Any of the non-wearable devices may be of a type enabled to communicate with an external device through a wired or wireless connection. In that case, one or more of the smart wearable devices may be enabled to communicate with one or more of the non-wearable devices by means of a direct wired or wireless connection 112. Further, one or more of the non-wearable devices may be of a type enabled to communicate with the network 102 through a standard wired or wireless connection 114. In that case, one or more of the smart wearable devices may be enabled to communicate with one or more of the non-wearable devices through the network 102.

One or more servers 116-1 through 116-n may be provided in a client-server configuration and connected to the network by means of a wired or wireless connection 118. The servers may include standalone servers, cluster servers, networked servers, or servers connected in an array to function like a large computer. In that case, one or more of the smart wearable devices may be enabled to communicate with one or more of the servers.

Figure 2:
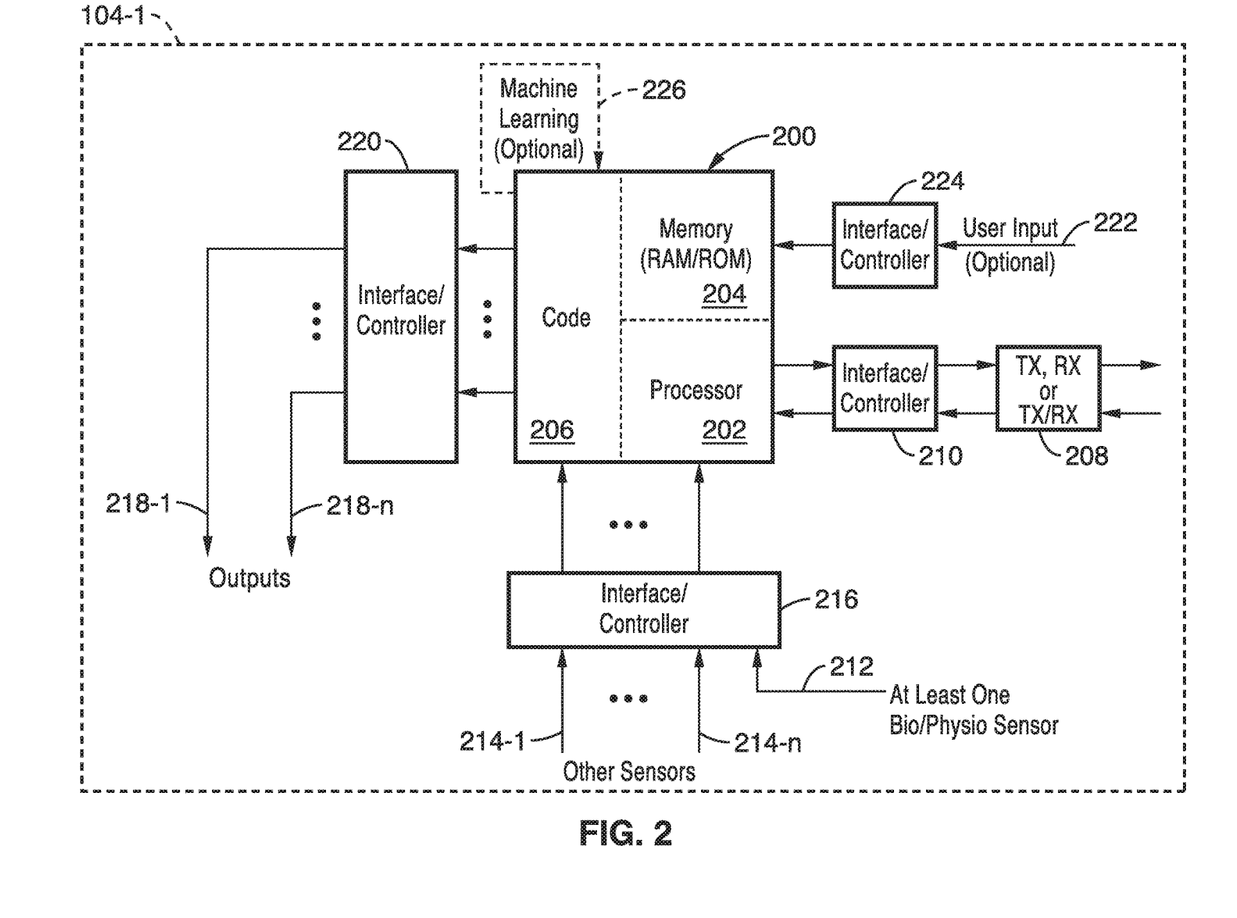
FIG. 2 is a functional block diagram of an embodiment of a smart wearable device described herein.

FIG. 2 illustrates a generalized embodiment of a smart wearable device according to the technology described herein. It will be appreciated that the embodiment shown may be modified or customized to enable performing the functions described herein. In the exemplary embodiment shown, the smart wearable device includes an "engine" 200 having a processor 202, memory 204, and application software code 206. The processor 202 can be any suitable conventional processor. The memory 204 may include any suitable conventional RAM type memory and/or ROM type memory with associated storage space for storing the application programming code 206.

A conventional wired or wireless communications module 208 (e.g., transmitter or receiver or transceiver) may be included as needed for performing one or more of the functions of the smart wearable device described herein. Examples of wireless communication capabilities that can be provided include, but are not limited to, Bluetooth, Wi-Fi, infrared, cellular, and near field communication. One or more conventional interfaces or controllers 210 may also be provided if needed. Examples of interfaces or controllers include, but are not limited to, analog to digital converters, digital to analog converters, buffers, etc.

The device may include at least one input 212 for a biological or physiological sensor for providing input to the device to perform one or more of the functions described herein. Sensor inputs 214-1 through 214-n for optional sensors may be included as well. These optional input sensors may include, but are not limited to, accelerometers, temperature sensors, altitude sensors, motion sensors, position sensors, and other sensors to perform the function(s) described herein. One or more conventional interfaces or controllers 216 may be provided if needed for the sensors. Examples of interfaces or controllers include, but are not limited to, analog to digital converters, digital to analog converters, buffers, etc.

Additionally, the device may include one or more outputs 218-1 through 218-n to drive one or more output devices (and include those output devices). These output devices may include, but are not limited to, haptic output devices, telemetry devices, visual devices, audible devices, and other output devices to perform the functions described herein. One or more conventional interfaces or controllers 220 may be provided if needed for the output devices. Examples of interfaces or controllers include, but are not limited to, analog to digital converters, digital to analog converters, buffers, etc.

A user input 222 may be provided according to the functions described herein. The user input may, for example, initiate one or more functions, terminate one or more functions, or intervene in a running process. The user input can be any conventional input device, including but not limited to, manual switches, touch sensors, magnetic sensors, proximity sensors, etc. One or more conventional interfaces or controllers 224 may be provided if needed for the output devices. Examples of interfaces or controllers include, but are not limited to, analog to digital converters, digital to analog converters, buffers, etc.

Depending on the function(s) described herein, the engine 200 may also include a feedback loop 226 for machine learning or other adaptive functions. The feedback loop may also provide for device calibration.

It will be appreciated that a smart wearable device as described herein would necessarily include a housing or carrier for the above-described components. It will further be appreciated that, as used herein, the term "smart wearable device" means a device that would be worn or otherwise associated with the body of a user and be "connected" to the user by means of at least one sensor for sensing one or more biological or physiological conditions of the user.

The particular form of the housing or carrier (i.e., wearable platform) can vary according to choice and suitability for performing the functions described herein. Examples of wearable platforms include, but are not limited to, hand worn devices, finger worn devices, wrist worn devices, head worn devices, arm worn devices, leg worn devices, angle worn devices, foot worn devices, toe worn devices, watches, eyeglasses, rings, bracelets, necklaces, articles of jewelry, articles of clothing, shoes, hats, contact lenses, gloves, etc.

It will further be appreciated that the input sensors and output devices may be integrated into the wearable platform, or may be external to the wearable platform, as is desired and/or suitable for the function(s) of the smart wearable device.

B. Smart Wearable Devices and System with Dynamic Control Over Power Consumption and Network Load.

Figure 3:
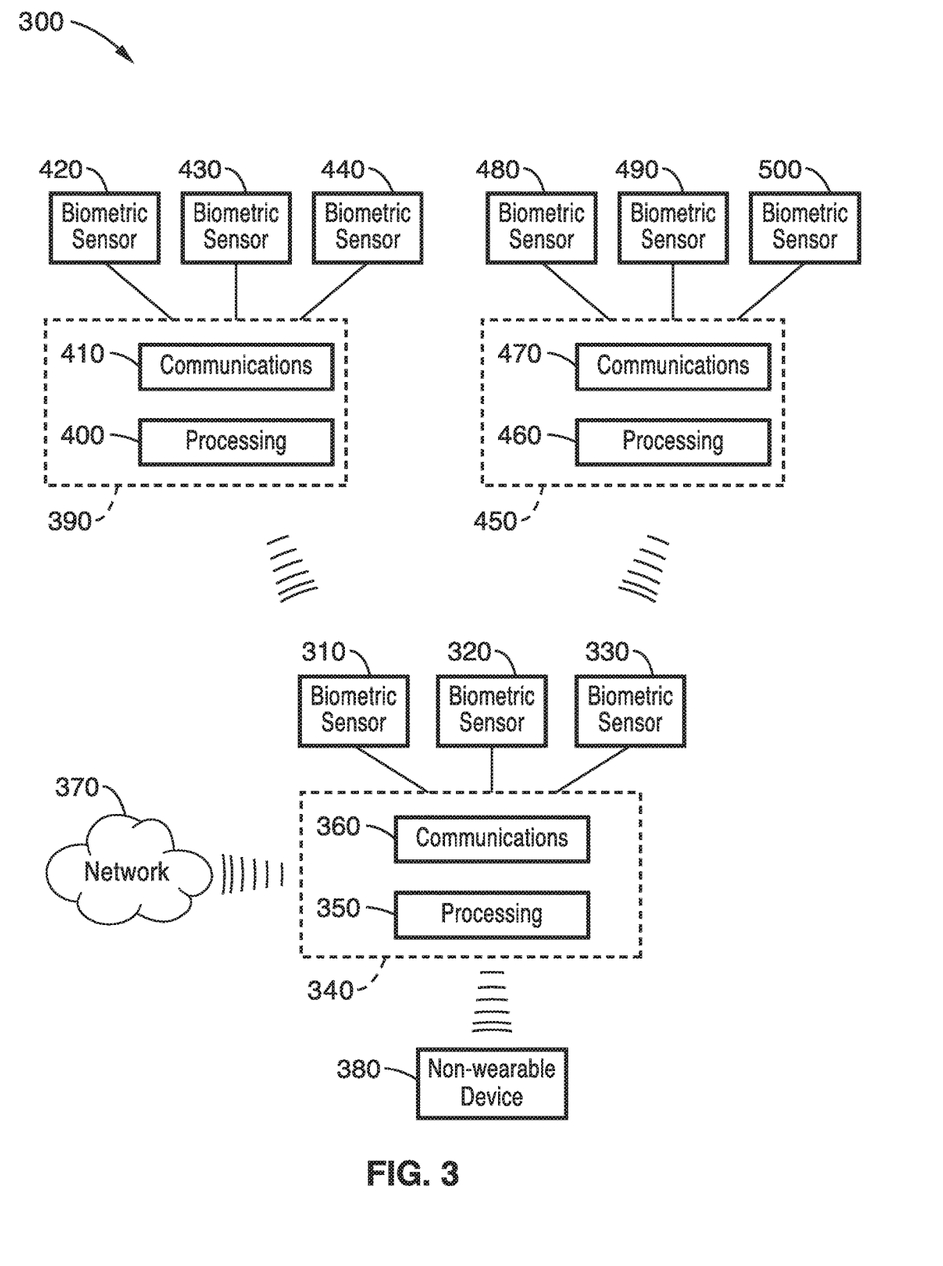
FIG. 3 is a functional block diagram on one configuration with a base and two satellite wearable sensor devices.

Referring now to FIG. 3, one embodiment 300 of a wearable base apparatus 340 is depicted schematically. The wearable base apparatus 340 may detect devices that are within the range of its communications link 360, such as the two non-wearable devices 390, 450 that can be coordinated by the base wearable apparatus upon communications between the devices. This may be accomplished by the smart wearable device pinging the non-wearable devices or determining Bluetooth or GPS signal strength or even Wi-Fi positioning.

The base 340 in this illustration is a wearable device with three biometric sensors 310, 320 and 330 that are worn by the user. The base 340 has a processor 350 and a communications link 360 that is configured to communicate wirelessly with the satellite sensor device 390 and satellite sensor device 450. The base apparatus 340 may optionally communicate with a non-wearable device 380 that has an interface as well as with a remote computer 370. Instructions, sensor data processing and recording may also take place on the remote computer 370.

Satellite sensor device 390 is a wearable sensor device that has a processor 400 and a communications link 410 that communicates with the base 340 in the embodiment shown in FIG. 3. The device has biometric sensors 420, 430 and 440 that sense selected physiological conditions of the user. The biometric sensors 420, 430 and 440 are preferably different than the biometric sensors of the base or the sensors 480, 490 and 500 of the second satellite wearable device 450. However, some of the sensors of the different wearable devices may have some redundancy.

Likewise, satellite sensor device 450 has a processor 460 and a communications link 470 to acquire and process sensor data from the biometric sensors 480, 490 and 500. The sensor data that is acquired can be processed by processor 460 and transferred to the base 340 through the communications link. Although only two satellite sensor devices are shown in FIG. 3, any number of satellite devices can be accommodated by the system.

The programming and the processor of the wearable devices can also monitor the battery power that is remaining in each device and the rate of power usage of the sensors that are present in each wearable sensor devices. Power consumption can also be monitored and controlled by the remote computer 370 through the base apparatus 340, in one embodiment. The battery power status of each of the wearable devices that are worn by the user and interconnected can be monitored and displayed to the user. The battery power usage of each of the monitored wearable devices can also be coordinated and optimized by turning off redundant sensors or reducing or cycling the "on" time of essential sensors.

Multiple wearable devices that are utilized by a user often have redundant sensors and may produce multiple flows of sensor data to be transferred to a remote computer over a communications network. One method 600 for optimizing power consumption and minimizing the sensor data transfer load of a network is shown in FIG. 4.

Figure 4:
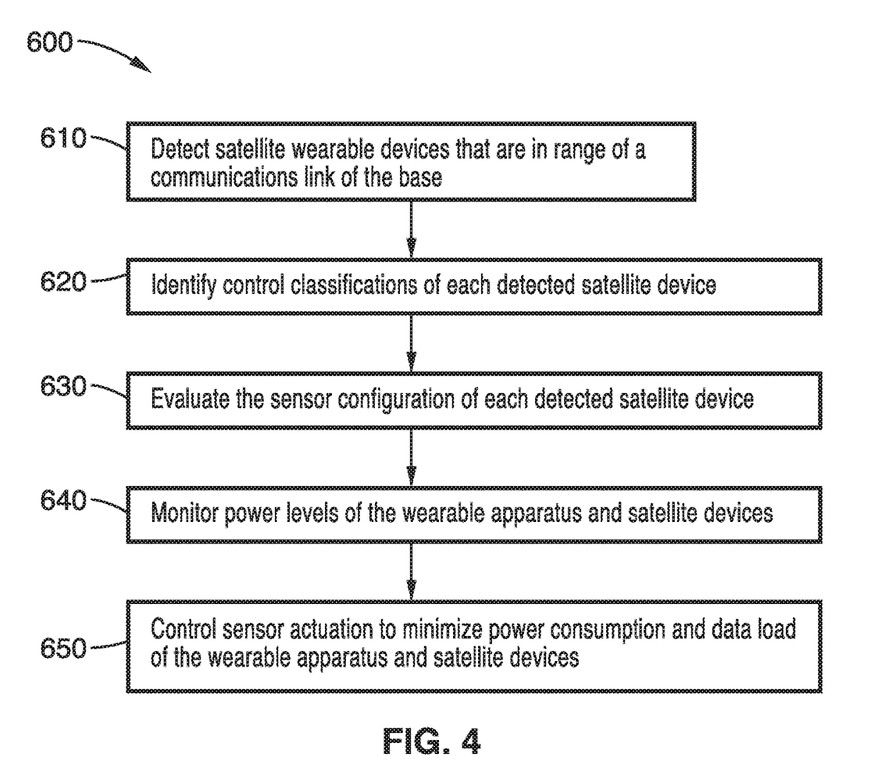
FIG. 4 is a functional flow diagram of one embodiment of the method for dynamic power consumption and network data load control.

At block 610 of FIG. 4, the base sensor detects any satellite sensor devices that may be in proximity to the base through the communications link. The base may have its own set of sensors or may simply be a command and transfer module with a processor, programming and communications link. The base may also detect non-wearable devices within the proximity of the base at block 610. In one embodiment, non-wearable devices may have sensors such as time, temperature or humidity sensors that can provide additional relevant sensor data. The non-wearable device with a user interface and communications link may also be configured to receive sensor data from the wearable sensor apparatus.

In another embodiment, the base device may authenticate access rights for each detected device as a security precaution over unintended access to the satellite sensor devices at block 610. The optional authentication is required before any control or transfer of sensor data can take place with the base.

The base communicates with each detected satellite sensor device to establish a link and identify the control classification that has been assigned to the device at block 620. This classification is one way to provide a control structure and priority between wearable devices. The base normally has the highest ranking so that all satellite sensor devices are subservient and allow control by the programming of the base apparatus. If the satellite classification exceeds that of the initially designated base, then the satellite device could become the base in one embodiment.

The classification of satellite sensor devices creates a central control over satellite devices (i.e. Master/Slave) type of architecture where one wearable device has priority/control delegation upon the other devices. However, other control architectures could also be used. For example, a parallel architecture can be used where all wearable devices sense equally and only the best/most accurate reading gets uploaded. Another type is a cluster architecture where multiple wearable devices get grouped together and each one is responsible for a specific subset of readings. A third type is a tree-like architecture where there is a delegation of authority (and power-on/power-off) at multiple levels.

The sensor configuration of each of the wearable sensor devices and base apparatus is evaluated for redundancy and sensitivity and block 630. Some wearable devices may have sensors that are the same. In this case sensor data from the same sensor types are processed and may be transferred for further evaluation by three different wearable devices. If each of three wearable devices has the same sensor then the sensing and processing of two are redundant, consume power and produce an excess transfer load. The sensors of the base and satellite devices may also be evaluated for sensitivity so that specific sensors can be activated and other less sensitive redundant sensors can be deactivated. If sensor sensitivity is not of interest then they may be deactivated in favor of a less sensitive sensor or one that consumes less power to use.

The power levels and capacity of each satellite device as well as the power consumption profile of its sensors are determined at block 640. The timing and duration of the activation of the selected sensors that are needed to produce the desired monitoring and sensing of the physical condition of the user can be optimized to minimize the power consumption of the devices over time. For example, wearable devices with sensors with a high power consumption profile can be actuated for short durations and then deactivated. Likewise, redundant sensors on a second satellite device can be activated in favor of a sensor on a satellite device that has a low current power level or low power capacity.

Accordingly, control over the sensor activation, power use and data transfer can be optimized at block 650 depending on the goals of the sensing of the wearable device in terms of sensitivity, data load and battery power consumption. In another embodiment, sensor redundancy is desirable so that control over the sensors takes priority over trying to minimize the power consumption of the devices.

Control over the sensors of the satellite devices and the base if it has them can also be performed by a remote computer or non-wearable device in some embodiments through wireless communications with the base of the group of wearable sensor devices. This configuration allows for remote control over the sensors of the user by a third party such as a medical care provider.

The system can be illustrated with a user with multiple wearable devices exercising at a gym. In this illustration, the application programming can be running on the engine 202, which monitors the wearer's physical activity. For example, the exercise monitor application program monitors sensor data including physical motion (by an accelerometer), location (GPS), time (a clock), heart beat by using multiple sensors on one or more of the three wearable devices in FIG. 3.

The application program that is running on the engine of the base wearable apparatus can processes the sensor data acquired from each of the wearable devices and can identify the type of the exercise. For example, using the GPS signal together with the map information which is downloaded from the servers, the application program can recognize where the user is located (e.g., at a swimming pool, at a gym, at a field, at home).

Similarly, if the application program determines that the user is at a gym and the user is running in place on a machine, then the application program decides the type of sensor data and the level of accuracy of that sensor data that is necessary to acquire. For example, when the user is running on a treadmill in the gym, the accurate GPS signal is not necessary because the user is unlikely to move away from the machine while running. However, accurate heart beat and motion information is needed because that information is useful to measure the strength of the exercise.

Once the sensor information needs are prioritized, the base wearable apparatus can communicate with other wearable devices to verify the accuracy of the sensor information of each wearable device and pick up the appropriate device for a particular type of sensor data. The other sensors can be turned off or turned to a low power mode to save power and avoid processing and transmitting redundant data streams. The desired processed sensor information can be provided to the user efficiently and the power demands from each of the devices can be optimized.

When the application program recognizes that the wearer has changed the type of exercise (e.g., from running on the machine to weight training), the application program can determine the type of the exercise and select appropriate sensor which is suitable for monitoring that type of exercise. For the application program to recognize that the wearer changes the type of exercise, the application program may receive the user input anytime (e.g. touching the particular place of the base wearable apparatus by the wearer).

In addition, the application program may detect a change in the signal pattern of the received sensor data to indicate a change. For example, the nature of the motion sensor information can change with the change in the type of exercise. For example, the motion sensor data will change when the wearer stops running and starts walking slowly and the heart does not beat as fast while walking as it does while running.

When changes in the sensor signal patterns by the application program are detected, the application program will turn on sensors that have been turned off or placed in a low power mode until the application program recognize the new type of exercise or activity of the wearer.

Although the application program was running on engine 202 of the wearable device in this illustration, the application program may be operated, in part, on the servers 116-1 to 116-n together with the locally running application program on the engine 202 to process sensor data. For example, the system may be configured to have the application program that is running on the servers do the heavy tasks that require large computing resources and the application program running locally on the engine 202 mainly collects sensor data and preliminary processes the sensor data, and then sends it to the servers.

Embodiments of the present technology may be described with reference to flowchart illustrations of methods and systems according to embodiments of the technology, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

It will further be appreciated that "programming" as used herein refers to one or more instructions that can be executed by a processor to perform a function as described herein. The programming can be embodied in software, in firmware, or in a combination of software and firmware. The programming can be stored local to the device in non-transitory media, or it can be stored remotely such as on a server, or all or a portion of the programming can be stored locally and remotely. Programming stored remotely can be downloaded (pushed) to the device by user initiation, or downloaded automatically based on one or more factors, such as, for example, location, a timing event, detection of an object, detection of a facial expression, detection of location, detection of a change in location, or other factors. It will further be appreciated that the terms processor, central processing unit (CPU), and computer are used synonymously to denote a device capable of executing the programming and communication with input/output interfaces and/or peripheral devices.

From the discussion above it will be appreciated that the technology can be embodied in various ways, including but not limited to the following:

1. A wearable sensor apparatus, comprising: (a) a computer processor with memory; (b) a plurality of sensors operably coupled to the processor; (c) a communications link; and (d) programming in a non-transitory computer readable medium and executable on the computer processor for performing steps comprising: (i) detecting satellite wearable devices that have one or more sensors that are in range of the communications link of the sensor apparatus; (ii) communicating with the one or more detected devices; (iii) identifying control classifications of each detected satellite device; (iv) establishing control of the apparatus and satellite devices based on the control classifications of the devices; (v) controlling sensor actuation of the sensor apparatus and satellite devices; and (vi) acquiring sensor data from selected sensors from one or more of the detected devices.

2. The apparatus of any previous embodiment 1, further comprising one or more output devices controlled by the processor.

3. The apparatus of any previous embodiment, wherein the programming further performs the steps comprising: notifying the wearer of the apparatus of detected satellite wearable devices through the output device on the wearable apparatus.

4. The apparatus of any previous embodiment, wherein the programming further performs the steps comprising: authenticating access rights for each detected device; and exchanging sensor data only with authenticated devices.

5. The apparatus of any previous embodiment, wherein the programming further performs the steps comprising: monitoring power levels of the wearable apparatus and satellite devices; and controlling sensor actuation to minimize power consumption of the wearable apparatus and satellite devices.

6. The apparatus of any previous embodiment, wherein the programming further performs the steps comprising: evaluating the sensor configuration of each detected device; selecting the most accurate sensor type of all sensor devices; and acquiring sensor data from the most accurate sensor.

7. The apparatus of any previous embodiment, wherein the programming further performs the steps comprising: evaluating the sensor configuration of each detected device; selecting only one of each sensor type from all sensor devices; and acquiring sensor data from only one sensor type from all of the sensors of the sensor apparatus and satellite sensor devices.

8. The apparatus of any previous embodiment, wherein the programming further performs the step comprising deactivating sensors that were not selected for actuation.

9. The apparatus of any previous embodiment, wherein the programming further performs the steps comprising: detecting non-wearable devices that have one or more sensors that are in range of the communications link of the sensor apparatus; and acquiring sensor data from the sensors of the detected non-wearable devices.

10. A wearable device sensor system, comprising: (a) at least one satellite sensor device, each device comprising: (i) a communications link; (ii) a computer processor with memory; (iii) a plurality of sensors operably coupled to the processor; and (iv) programming in a non-transitory computer readable medium and executable on the computer processor for performing steps comprising: 1. sending and receiving communications from a wearable sensor device; and 2. processing sensor data received from the wearable sensor; and (b) a wearable sensor apparatus, comprising: (i) a computer processor with memory; (ii) a plurality of sensors operably coupled to the processor; (iii) a communications link; and (iv) programming in a non-transitory computer readable medium and executable on the computer processor for performing steps comprising: 1. detecting satellite wearable devices that have one or more sensors that are in range of the communications link of the sensor apparatus; 2. communicating with the one or more detected devices; 3. identifying control classifications of each detected satellite device; 4. establishing control of the apparatus and satellite devices based on the control classifications of the devices; 5. controlling sensor actuation of the sensor apparatus and satellite devices; and 6. acquiring sensor data from selected sensors from one or more of the detected devices.

11. The system of any previous embodiment, further comprising: a non-wearable device with a user interface and communications link configured to receive sensor data from the wearable sensor apparatus.

12. The system of any previous embodiment, wherein the wearable sensor apparatus programming further performs the steps comprising: monitoring power levels of the wearable apparatus and satellite devices; and controlling sensor actuation to minimize power consumption of the wearable apparatus and satellite devices.

13. The system of any previous embodiment, wherein the wearable sensor apparatus programming further performs the steps comprising: evaluating the sensor configuration of each detected device; selecting the most accurate sensor type of all sensor devices; and acquiring sensor data from the most accurate sensor.

14. The system of any previous embodiment, wherein the wearable sensor apparatus programming further performs the steps comprising: evaluating the sensor configuration of each detected device; selecting only one of each sensor type from all sensor devices; acquiring sensor data from only one sensor type from all of the sensors of the sensor apparatus and satellite sensor devices; and deactivating sensors that were not selected for actuation.

15. The system of any previous embodiment, wherein the wearable sensor apparatus programming further performs the steps comprising: authenticating access rights for each detected device; and exchanging sensor data only with authenticated devices.

16. A computer implemented method for optimization of device power consumption and network load with wearable devices, the method comprising: detecting satellite wearable devices that have one or more sensors that are in range of a communications link of a sensor apparatus; communicating with the one or more detected devices; identifying control classifications of each detected satellite device; establishing control of sensor apparatus over detected satellite devices based on the control classifications of the devices; controlling sensor actuation of sensor apparatus and satellite devices; and acquiring sensor data from sensors from one or more of the detected devices.

17. The method of any previous embodiment, further comprising: monitoring power levels of the wearable apparatus and satellite devices; and controlling sensor actuation to minimize power consumption of the wearable apparatus and satellite devices.

18. The method of any previous embodiment, further comprising: evaluating the sensor configuration of each detected satellite device; selecting the most accurate sensor type of all sensor devices; and acquiring sensor data from the most accurate sensor.

19. The method of any previous embodiment, further comprising: evaluating the sensor configuration of each detected device; selecting only one of each sensor type from all sensor devices; acquiring sensor data from only one sensor type from all of the sensors of the sensor apparatus and satellite sensor devices; and deactivating sensors that were not selected for actuation.

20. The method of any previous embodiment, further comprising: detecting non-wearable devices that have one or more sensors that are in range of the communications link of the sensor apparatus; and acquiring sensor data from the sensors of the detected non-wearable devices.

Although the description above contains many details, these should not be construed as limiting the scope of the technology but as merely providing illustrations of some of the presently preferred embodiments of this technology. Therefore, it will be appreciated that the scope of the present technology fully encompasses other embodiments which may become obvious to those skilled in the art, and that the scope of the present technology is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present technology, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112 unless the element is expressly recited using the phrase "means for" or "step for".

What is claimed is:

1. A wearable sensor apparatus, comprising:
   (a) a computer processor with memory;
   (b) a plurality of sensors operably coupled to the processor;
   (c) a communications link; and
   (d) programming in a non-transitory computer readable medium and executable on the computer processor for performing steps comprising:
      (i) detecting satellite wearable devices that have one or more sensors that are in range of the communications link of the sensor apparatus;
      (ii) authenticating access rights for each detected device;
      (iii) communicating with the one or more detected devices;
      (iv) identifying control classifications of each detected satellite device;
      (v) establishing control of the apparatus and satellite devices based on the control classifications of the devices;
      (vi) controlling sensor actuation of the sensor apparatus and satellite devices; and
      (vii) acquiring sensor data from selected sensors from one or more of the detected devices that have been authenticated.

2. An apparatus as recited in claim 1, further comprising one or more output devices controlled by the processor.

3. An apparatus as recited in claim 2, wherein said programming further performs the steps comprising:
   notifying the wearer of the apparatus of detected satellite wearable devices through the output device on the wearable apparatus.

4. An apparatus as recited in claim 1, wherein said programming further performs the steps comprising:
   monitoring power levels of the wearable apparatus and satellite devices; and
   controlling sensor actuation to minimize power consumption of the wearable apparatus and satellite devices.

5. An apparatus as recited in claim 1, wherein said programming further performs the steps comprising:
   evaluating the sensor configuration of each detected device;
   selecting the most accurate sensor type of all sensor devices; and
   acquiring sensor data from the most accurate sensor.

6. An apparatus as recited in claim 1, wherein said programming further performs the steps comprising:
   evaluating the sensor configuration of each detected device;
   selecting only one of each sensor type from all sensor devices; and
   acquiring sensor data from only one sensor type from all of the sensors of the sensor apparatus and satellite sensor devices.

7. An apparatus as recited in claim 6, wherein said programming further performs the step comprising deactivating sensors that were not selected for actuation.

8. An apparatus as recited in claim 1, wherein said programming further performs the steps comprising:
   detecting non-wearable devices that have one or more sensors that are in range of the communications link of the sensor apparatus; and
   acquiring sensor data from the sensors of the detected non-wearable devices.

9. A wearable device sensor system, comprising:
   (a) at least one satellite sensor device, each device comprising:
      (i) a communications link;
      (ii) a computer processor with memory;
      (iii) a plurality of sensors operably coupled to the processor; and
      (iv) programming in a non-transitory computer readable medium and executable on the computer processor for performing steps comprising:
         1. sending and receiving communications from a wearable sensor device; and
         2. processing sensor data received from the wearable sensor; and
   (b) a wearable sensor apparatus, comprising:
      (i) a computer processor with memory;
      (ii) a plurality of sensors operably coupled to the processor;
      (iii) a communications link; and
      (iv) programming in a non-transitory computer readable medium and executable on the computer processor for performing steps comprising:
         1. detecting satellite wearable devices that have one or more sensors that are in range of the communications link of the sensor apparatus;

2. communicating with the one or more detected devices;
3. identifying control classifications of each detected satellite device;
4. evaluating the sensor configuration of each detected device;
5. selecting the most accurate sensor type of all sensor devices;
6. establishing control of the apparatus and satellite devices based on the control classifications of the devices;
7. controlling sensor actuation of the sensor apparatus and satellite devices; and
8. acquiring sensor data from selected sensors from one or more of the detected devices.

10. The system as recited in claim 9, further comprising:
a non-wearable device with a user interface and communications link configured to receive sensor data from the wearable sensor apparatus.

11. The system as recited in claim 9, wherein said wearable sensor apparatus programming further performs the steps comprising:
monitoring power levels of the wearable apparatus and satellite devices; and
controlling sensor actuation to minimize power consumption of the wearable apparatus and satellite devices.

12. The system as recited in claim 9, wherein said wearable sensor apparatus programming further performs the steps comprising:
selecting only one of each sensor type from all sensor devices;
acquiring sensor data from only one sensor type from all of the sensors of the sensor apparatus and satellite sensor devices; and
deactivating sensors that were not selected for actuation.

13. The system as recited in claim 9, wherein said wearable sensor apparatus programming further performs the steps comprising:
authenticating access rights for each detected device; and
exchanging sensor data only with authenticated devices.

14. A computer implemented method for optimization of device power consumption and network load with wearable devices, the method comprising:
detecting satellite wearable devices that have one or more sensors that are in range of a communications link of a sensor apparatus;
communicating with the one or more detected devices;
identifying control classifications of each detected satellite device;
evaluating the sensor configuration of each detected satellite device;
selecting the most accurate sensor type of all sensor devices;
establishing control of sensor apparatus over detected satellite devices based on the control classifications of the devices;
controlling sensor actuation of sensor apparatus and satellite devices; and
acquiring sensor data from the most accurate sensors from one or more of the detected devices.

15. The method as recited in claim 14, further comprising:
monitoring power levels of the wearable apparatus and satellite devices; and
controlling sensor actuation to minimize power consumption of the wearable apparatus and satellite devices.

16. The method as recited in claim 14, further comprising:
selecting only one of each sensor type from all sensor devices;
acquiring sensor data from only one sensor type from all of the sensors of the sensor apparatus and satellite sensor devices; and
deactivating sensors that were not selected for actuation.

17. The method as recited in claim 14, further comprising:
detecting non-wearable devices that have one or more sensors that are in range of the communications link of the sensor apparatus; and
acquiring sensor data from the sensors of the detected non-wearable devices.

* * * * *